(12) United States Patent
Lin

(10) Patent No.: US 11,633,187 B2
(45) Date of Patent: Apr. 25, 2023

(54) VASCULAR ANASTOMOSIS DEVICE

(71) Applicant: Hsiu-Feng Lin, Taipei (TW)

(72) Inventor: Hsiu-Feng Lin, Taipei (TW)

(*) Notice: Subject to any disclaimer, the term of this patent is extended or adjusted under 35 U.S.C. 154(b) by 281 days.

(21) Appl. No.: 17/197,086

(22) Filed: Mar. 10, 2021

(65) Prior Publication Data
US 2021/0282778 A1  Sep. 16, 2021

(30) Foreign Application Priority Data

Mar. 13, 2020  (TW) .................................. 109108309

(51) Int. Cl.
*A61B 17/11* (2006.01)

(52) U.S. Cl.
CPC ........ *A61B 17/11* (2013.01); *A61B 2017/1107* (2013.01); *A61B 2017/1132* (2013.01)

(58) Field of Classification Search
CPC .................. A61B 17/11; A61B 17/115; A61B 2017/00473; A61B 2017/1132; A61B 2017/1107
See application file for complete search history.

(56) References Cited

U.S. PATENT DOCUMENTS

| | | | | |
|---|---|---|---|---|
| 5,904,697 | A | * | 5/1999 | Gifford, III ...... A61B 17/12109 606/155 |
| 2008/0269784 | A1 | * | 10/2008 | Abbott .................... A61B 17/11 606/167 |
| 2015/0245839 | A1 | * | 9/2015 | Wirtel, III .......... A61B 17/0643 606/153 |

* cited by examiner

*Primary Examiner* — Brooke Labranche
*Assistant Examiner* — Moira E Hayes
(74) *Attorney, Agent, or Firm* — Bacon & Thomas, PLLC

(57) ABSTRACT

A vascular anastomosis device includes a vascular fastener having a first ring and a second ring, and a vascular fastening mechanism. The first ring is provided a first groove and the second ring is provided with a first projection. In addition, the vascular fastener is disposed in the vascular fastening mechanism. The vascular fastening mechanism includes a first tube, a vascular supporting unit, an advancing ring, a third tube, and a spreading unit. The first tube is connected with a second tube. The vascular supporting unit is disposed in the second tube. Furthermore, the vascular supporting unit includes a vascular supporting body and a vascular spreader assembled on the vascular supporting body. The first ring, the second ring, and the advancing ring are assembled on the second tube. The third tube is disposed in the first tube. The spreading unit is disposed in the third tube.

18 Claims, 16 Drawing Sheets

VASCULAR ANASTOMOSIS DEVICE

CROSS REFERENCE TO RELATED APPLICATION

This application claims the benefits of the Taiwan Patent Application Serial Number 109108309, filed on Mar. 13, 2020, the subject matter of which is incorporated herein by reference.

BACKGROUND OF THE INVENTION

1. Field of the Invention

The present invention relates to a vascular anastomosis device.

2. Description of Related Art

Vascular anastomosis is a major advancement in microsurgery, which can effectively connect blood vessels and plays a key role in the microscopic repair and reconstruction. Nowadays, in addition to traditional suture, new vascular anastomosis techniques are also booming, for example, sleeving suturing, adhesion, anastomotic clip or vascular stapler. Among them, it has been proved that vascular stapler technique can be widely applied on the limbs, breast, or oral and maxillofacial tissues, thereby proceeding repair and reconstruction to help the patients obtain the better therapeutic effects.

However, for conventional vascular stapler technique, it is necessary to manually use a vascular clamp to turn the blood vessel wall outward by 90 degrees, and then fix the turned-out blood vessel wall to the nail in a specific order. However, this step highly relies on the surgeon's skill. Also, it will be more difficult to perform this step if the patient's blood vessel is hardened or fragile, and it is easy to damage the blood vessel due to the uneven force. In addition, it is difficult to ensure that the blood vessel wall is properly fixed even if this step is completed. Therefore, manually using the vascular stapler in a conventional way still has problems such as poor fixation effect, easy to leak blood from the pinhole, time-consuming, or poor alignment, which needs to be improved. Furthermore, it is also impossible to ensure the consistency of the fixation effect of the manually applied stapler, so the fixed blood vessel may be detached in the patient's body, causing additional risks for the operation.

Therefore, there is an urgent need to propose an improved vascular anastomosis device to eliminate or alleviate the above-mentioned problems.

SUMMARY OF THE INVENTION

In view of this, according to an aspect of the present invention, a vascular anastomosis device is provided to improve the fixation effect of the vascular anastomosis device, shorten the operation time, reduce the alignment time, or improve the convenience of use, so that the vascular anastomosis device can perform greater utility to reduce the burden on surgeons, or even reduce the additional risks of surgery.

Therefore, the vascular anastomosis device of the present invention comprises a vascular fastener and a vascular fastening mechanism; wherein, the vascular fastener comprises a first ring and a second ring, and the first ring is provided with a first groove, the second ring is provided with a first projection, and the first groove corresponds to the first projection, thereby allowing the first ring engaging with the second ring through the engagement between the first groove and the first projection. In addition, the vascular fastener is disposed in the vascular fastening mechanism, so the blood vessel can be fixed on the vascular fastener by operating the vascular fastening mechanism.

In addition, the vascular fastening mechanism comprises a first tube, a vascular supporting unit, an advancing ring, a third tube, and a spreading unit; wherein a first end of the first tube is connected to a second tube; and, the vascular supporting unit is disposed at the other end of the second tube opposite to the end connected to the first tube. The vascular supporting unit comprises a vascular supporting body and a vascular spreader assembled on the vascular supporting body. By moving the spreading unit forward, the vascular spreader can be expanded to turn the blood vessel outward by an angle, such as 90 degrees, and the outwardly turned blood vessel can be attached to the first ring. The first ring, the second ring, and the advancing ring are disposed on the second tube and between the vascular supporting unit and the first end, wherein the second ring is located between the first ring and the advancing ring, the first ring is located between the vascular supporting unit and the second ring, the advancing ring is located between the second ring and the first end, and the advancing ring can be moved forward, allowing the second ring engaging with the first ring. The third tube is disposed in the first tube and protruding from the first end, wherein the second tube, the first ring, the second ring and the advancing ring are disposed in the third tube. The spreading unit is disposed in the third tube, and one end of the spreading unit is adjacent to the vascular spreader. Therefore, when the spreading unit is moved forward, it can provide the vascular spreader with an outward expansion force to turn the blood vessel outward by an angle, such as 90 degrees, and the outwardly turned blood vessel can be attached to the first ring.

In the vascular anastomosis device of the present invention, the vascular fastening mechanism may further comprise a first advancing tube disposed in the third tube, and the spreading unit is disposed in the first advancing tube. However, the present invention is not limited thereto.

In the vascular anastomosis device of the present invention, the vascular fastening mechanism may further comprise a second advancing tube, the second advancing tube is disposed in the third tube, the spreading unit is disposed in the second advancing tube, and the second advancing tube is located between the first advancing tube and the first end. However, the present invention is not limited thereto.

In the vascular anastomosis device of the present invention, a first elastic element may be further disposed on an inner tube wall of the first advancing tube, the first elastic element is disposed between the spreading unit and the first advancing tube; wherein, the first elastic element may be an elastic piece, and the first elastic element can clamp or loosen the spreading unit thereby. However, the present invention is not limited thereto.

In the vascular anastomosis device of the present invention, the vascular fastening mechanism may further comprise an engaging member assembled on an outer sidewall of the third tube, the engaging member has a first flange, and the first ring, the second ring and the advancing ring are fixed in the third tube through the first flange. However, the present invention is not limited thereto.

In the vascular anastomosis device of the present invention, a through hole may be provided on a tube wall of the third tube, and the engaging member has a first protrusion disposed in the through hole. However, the present invention is not limited thereto.

In the vascular anastomosis device of the present invention, the through hole of the third tube may comprise a second protrusion, the first protrusion has a first recess, and the first recess and the second protrusion are arranged correspondingly. However, the present invention is not limited thereto.

In the vascular anastomosis device of the present invention, the vascular fastening mechanism may further comprise a second elastic element, and the second elastic element is disposed on an outer sidewall of the second tube and connected with the advancing ring. Furthermore, the second elastic element may be a spring, so that the advancing ring springs the vascular fastener outward with the elastic force provided by the second elastic element, when the engaging element springs outward. However, the present invention is not limited thereto.

In the vascular anastomosis device of the present invention, it may further comprise a housing, wherein an advancing unit is disposed in the housing, the vascular fastening mechanism is disposed in the housing, and the advancing unit and a second end of the first tube are disposed correspondingly. However, the present invention is not limited thereto.

In the vascular anastomosis device of the present invention, it may further comprise a housing, wherein an advancing unit is disposed in the housing, the vascular fastening mechanism is disposed in the housing, and the advancing unit and the first advancing tube are disposed correspondingly. However, the present invention is not limited thereto.

In the vascular anastomosis device of the present invention, the advancing unit has a third protrusion, the first advancing tube has a second recess, and the third protrusion corresponds to the second recess. However, the present invention is not limited thereto.

In the vascular anastomosis device of the present invention, a third elastic element is further disposed in the housing, and the first tube is disposed between the third elastic element and the advancing unit, wherein the third elastic element may be a spring. However, the present invention is not limited thereto.

In the vascular anastomosis device of the present invention, it may further comprise a holding unit, wherein the holding unit is located in the housing and connected to the advancing unit. Therefore, the advancing unit can be driven by operating the holding unit. However, the present invention is not limited thereto.

In the vascular anastomosis device of the present invention, a fourth tube may be further disposed in the housing, and the advancing unit is disposed in the fourth tube; wherein, the fourth tube has a first track, and the advancing unit has a fourth protrusion disposed on the first track. However, the present invention is not limited thereto.

In the vascular anastomosis device of the present invention, the first advancing tube has a second flange, a groove is provided on the inner tube wall of the third tube, and the second flange corresponds to the groove. However, the present invention is not limited thereto.

In the vascular anastomosis device of the present invention, a plurality of connecting walls may be further disposed on the first ring, and two adjacent walls of the plurality of connecting walls are arranged in an interval. However, the present invention is not limited thereto.

In the vascular anastomosis device of the present invention, the width of the interval may be substantially the same as that of one of the plurality of connecting walls. However, the present invention is not limited thereto.

In the vascular anastomosis device of the present invention, a second groove is provided on a sidewall of one of the plurality of connecting walls facing the second ring. However, the present invention is not limited thereto.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
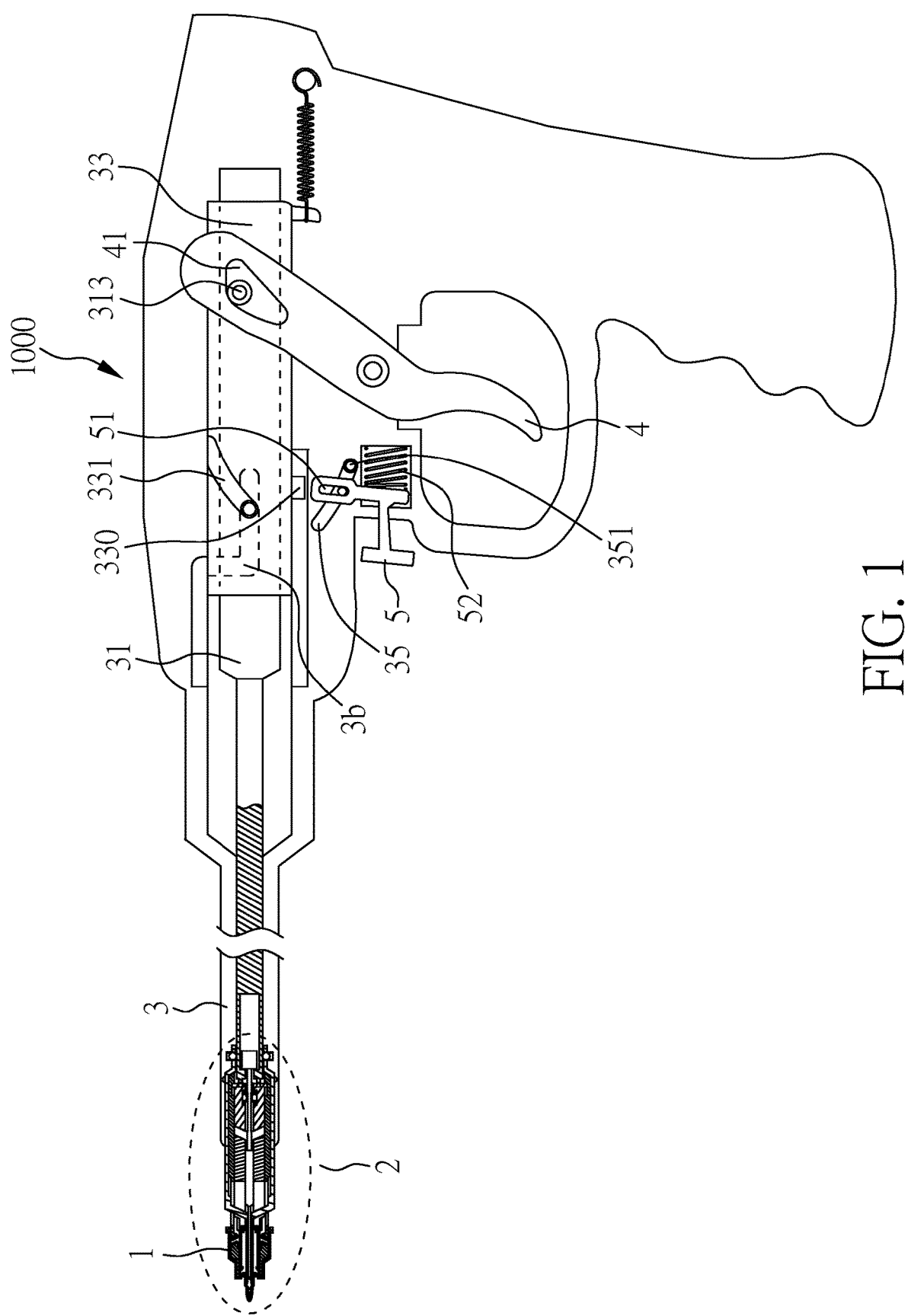
FIG. 1 shows a schematic diagram of a vascular anastomosis device according to an embodiment of the present invention.

Different embodiments of the present invention are provided in the following description. These embodiments are meant to explain the technical content of the present invention, but not meant to limit the scope of the present invention. A feature described in an embodiment may be applied to other embodiments by suitable modification, substitution, combination, or separation.

It should be noted that, in the present specification, when a component is described to have an element, it means that the component may have one or more of the elements, and it does not mean that the component has only one of the elements, except otherwise specified.

Moreover, in the present specification, the ordinal numbers, such as "first" or "second", are used to distinguish a plurality of elements having the same name, and it does not mean that there is essentially a level, a rank, an executing order, or an manufacturing order among the elements, except otherwise specified. A "first" element and a "second" element may exist together in the same component, or alternatively, they may exist in different components, respectively. The existence of an element described by a greater ordinal number does not essentially means the existent of another element described by a smaller ordinal number.

Moreover, in the present specification, the terms, such as "top", "bottom", "left", "right", "front", "back", or "middle", as well as the terms, such as "on", "above", "under", "below", or "between", are used to describe the relative positions among a plurality of elements, and the described relative positions may be interpreted to include their translation, rotation, or reflection.

Moreover, in the present specification, when an element is described to be arranged "on" another element, it does not essentially means that the elements contact the other element, except otherwise specified. Such interpretation is applied to other cases similar to the case of "on".

Moreover, in the present specification, the terms, such as "preferably" or "advantageously", are used to describe an optional or additional element or feature, and in other words, the element or the feature is not an essential element, and may be ignored in some embodiments.

Moreover, in the present specification, when an element is described to be "suitable for" or "adapted to" another element, the other element is an example or a reference helpful in imagination of properties or applications of the element, and the other element is not to be considered to form a part of a claimed subject matter; similarly, except otherwise specified; similarly, in the present specification, when an element is described to be "suitable for" or "adapted to" a configuration or an action, the description is made to focus on properties or applications of the element, and it does not essentially mean that the configuration has been set or the action has been performed, except otherwise specified.

Moreover, in the present specification, a value may be interpreted to cover a range within ±10% of the value, and in particular, a range within +5% of the value, except otherwise specified.

Structure of Vascular Anastomosis Device

FIG. 1 shows a schematic diagram of a vascular anastomosis device according to an embodiment of the present invention.

Figures 3A, 3B:
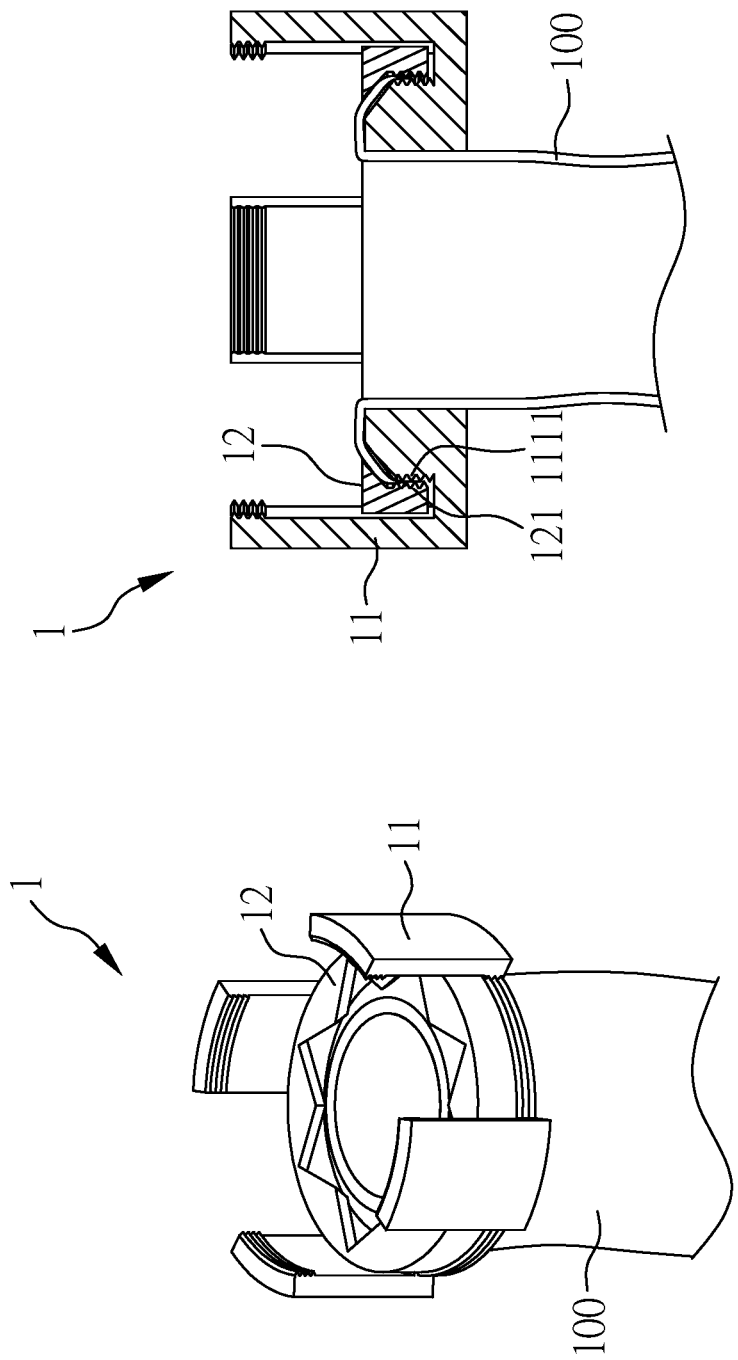
FIG. 3A to FIG. 3B show perspective views of a vascular fastener according to an embodiment of the present invention.
Figures 4A, 4B:
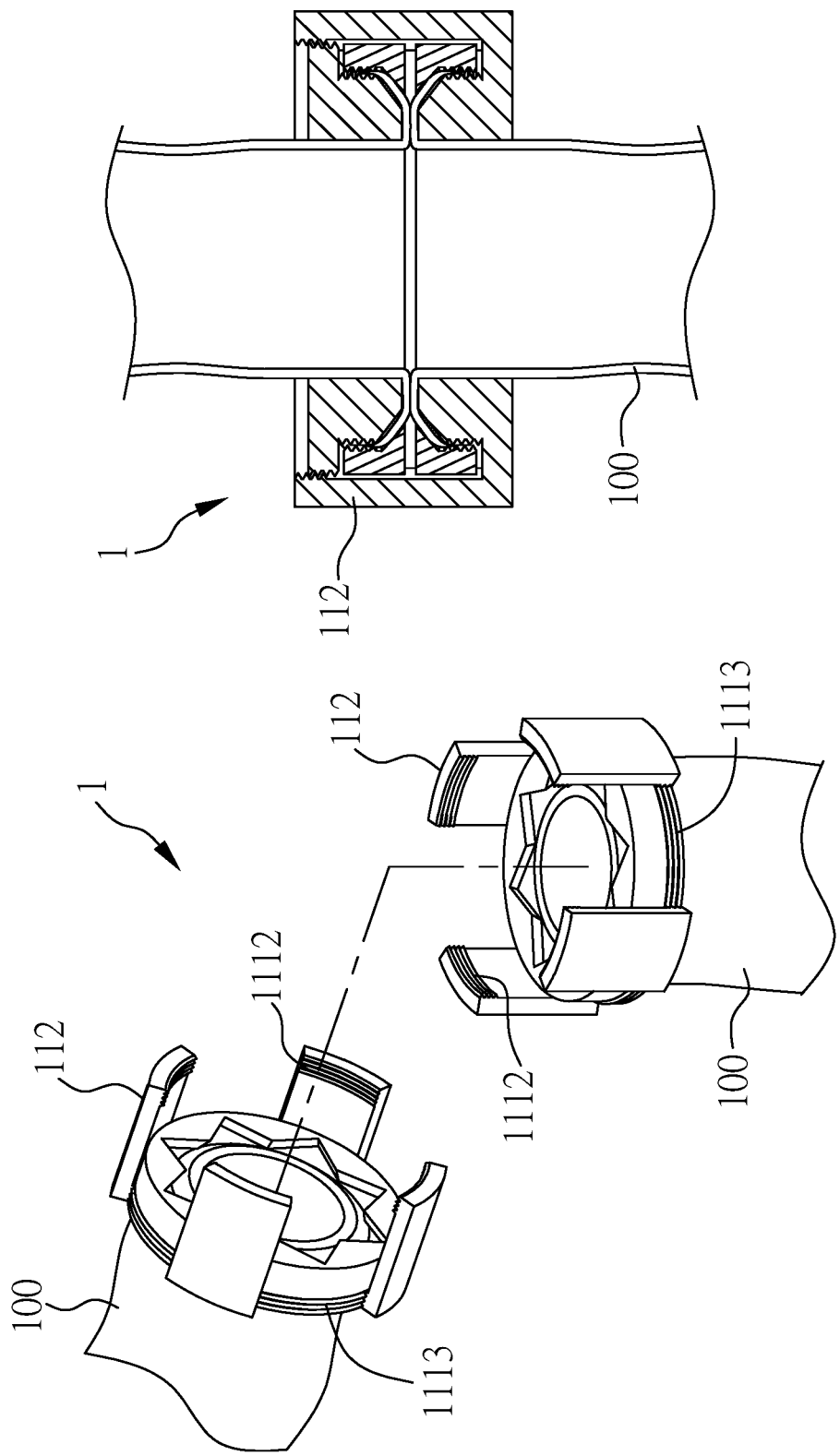
FIG. 4A to FIG. 4B show perspective views of a vascular fastener according to an embodiment of the present invention.
Figure 10:
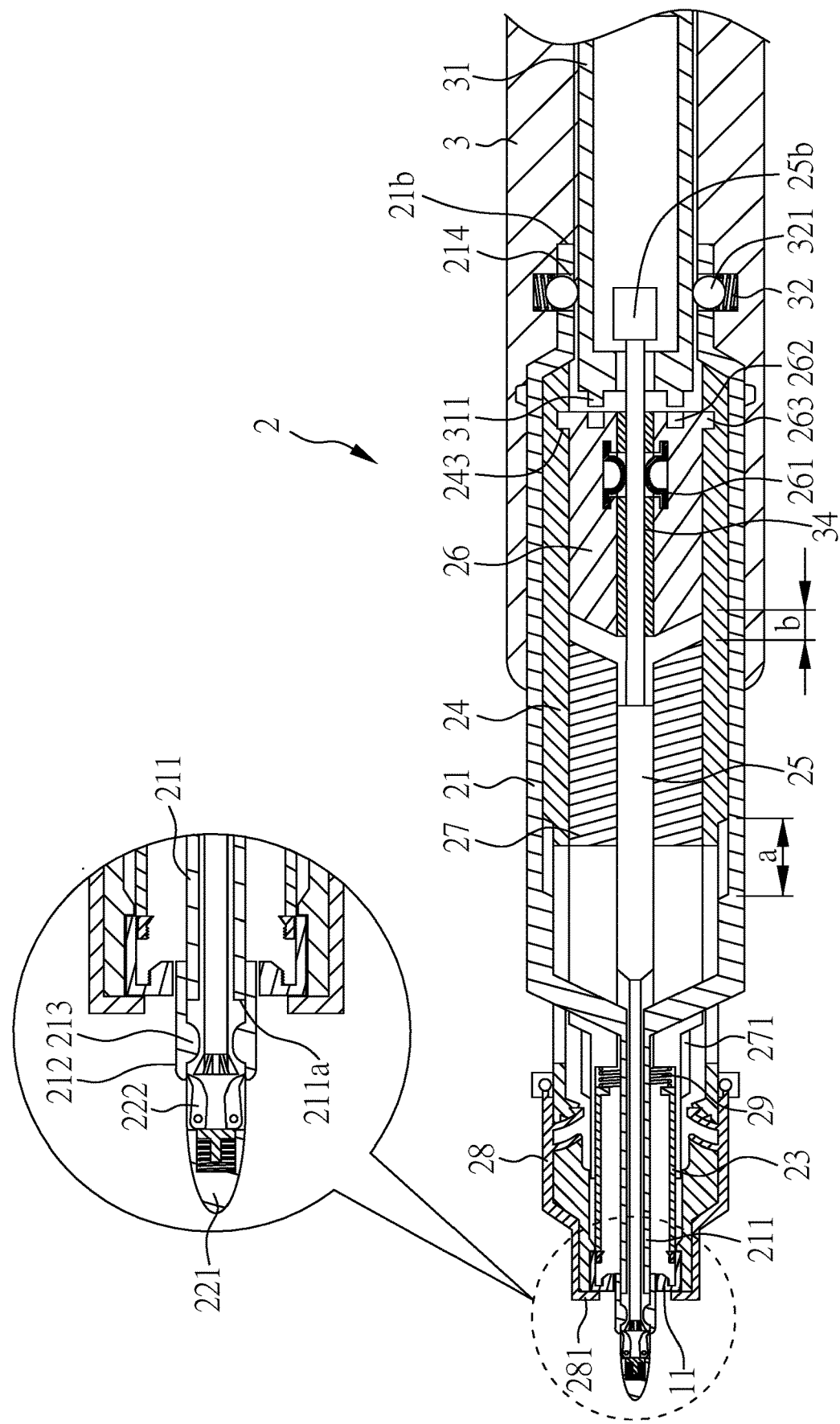
FIG. 10 to FIG. 16 show schematic diagrams of the operating mechanism of the vascular anastomosis device according to an embodiment of the present invention.
Figure 11:
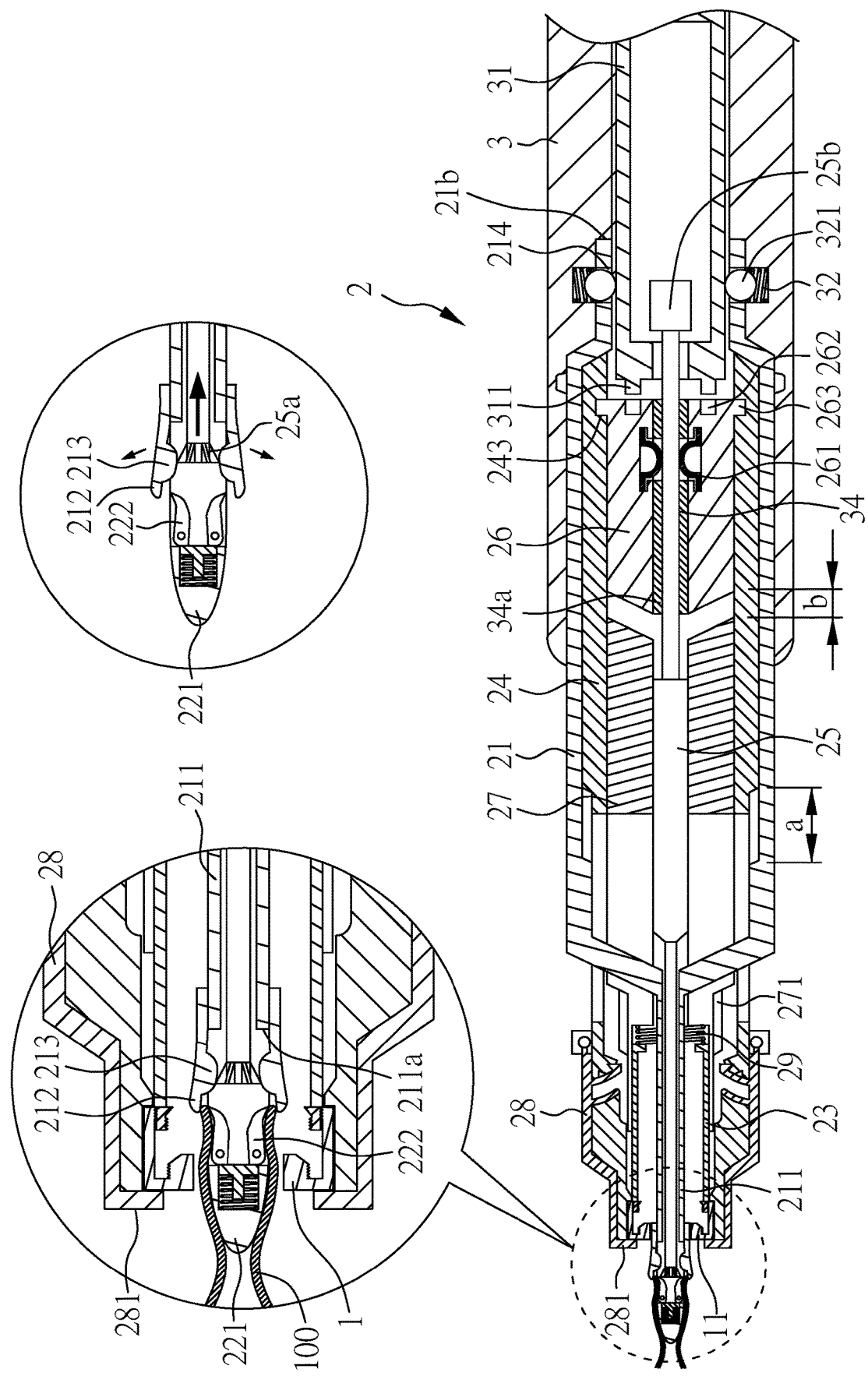

As shown in FIG. 1, the vascular anastomosis device 1000 of the present embodiment includes: a vascular fastener 1, a vascular fastening mechanism 2, a housing 3, an advancing unit 31, a holding unit 4, and a movable unit 5, wherein the advancing unit 31 is disposed in the housing 3, the vascular fastening mechanism 2 is disposed in the housing 3, and the holding unit 4 is partially located in the housing 3 and connected to the advancing unit 31. In addition, the holding unit 4 has a through hole 41, an interlocking unit 313 is disposed on the outer sidewall of the advancing unit 31, and the interlocking unit 313 is provided in the through hole 41. The movable unit 5 is provided with a through hole 51, and the housing 3 is provided with an interlocking rod 35, in which a shaft 351 is disposed on the rear end of the interlocking rod 35, that is, near the fourth elastic element 52. The interlocking rod 35 rotates with the shaft 351 as the center when operating the movable unit 5, so that the interlocking rod 35 contacts a first bump 330 located under the fourth tube 33 to interlock the advancing unit 31 and then the spreading unit 25 is driven to move backwards. Therefore, the first end 25a of the spreading unit 25 can contact a bulge 213, then an elastic body 212 is pushed out to form a gap and the vascular supporting body 221 is inserted into the blood vessel 100 simultaneously, thereby clamping the blood vessel 100, as shown in FIG. 11. Furthermore, the movable unit 5 can be repeatedly operated until the blood vessel 100 is clamped in the elastic body 212 in a correct manner, as shown in FIG. 11. In addition, because the movable unit 5 is connected to the fourth elastic element 52, the movable unit 5 can be moved back to the initial position and the spreading unit 25 can also be moved back to its initial position when stopping the operation of the movable unit 5 (as shown in FIG. 10), thereby facilitating the repeated operation. Furthermore, when the holding unit 4 is operated, the interlocking unit 313 moves along the wall of the through hole 41 to drive the advancing unit 31 to actuate the vascular fastening mechanism 2 in the housing 3, thereby fixing one end of the blood vessel 100 to the vascular fastener 1 (as shown in FIG. 2A and FIG. 3A); and, the other end of the blood vessel 100 can be fixed to another vascular fastener 1 (as shown in FIG. 2A and FIG. 3A) by repeating the same steps. Then, the two vascular fasteners 1 in which blood vessel 100 fixed (as shown in FIG. 2A, FIG. 4A, and FIG. 4B) are engaged with each other, so that the blood vessel 100 can be connected in an efficient or simple manner, and the manual anastomosis is not desired for the blood vessel 100.

Figure 2B:
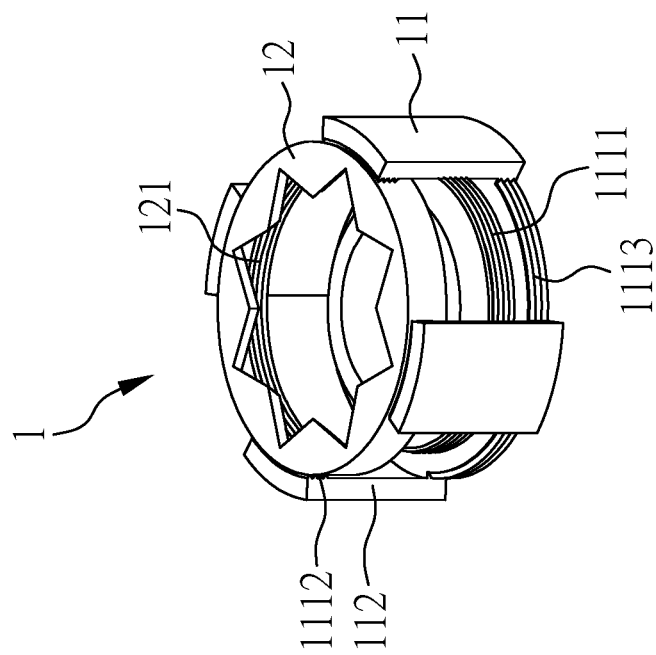
FIG. 2A to FIG. 2B show perspective views of a vascular fastener according to an embodiment of the present invention.
Figure 2A:
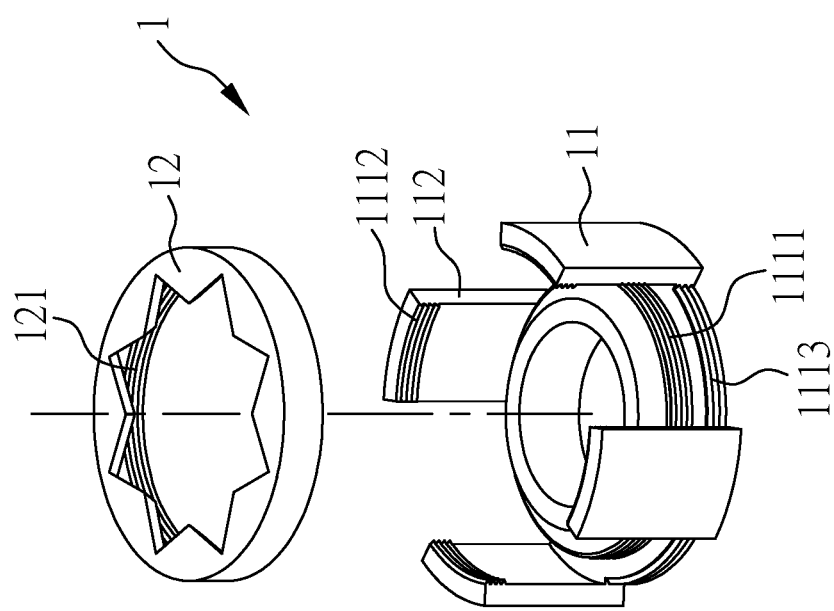

FIG. 2A to FIG. 2B show perspective views of a vascular fastener according to an embodiment of the present invention.

As shown in FIG. 2A to FIG. 2B (the blood vessel 100 is not fixed to the vessel fastener 1), the vascular fastener 1 of the present embodiment comprises a first ring 11 and a second ring 12, and the first ring 11 is provided with a first groove 1111, the second ring 12 is provided with a first projection 121, and the first groove 1111 corresponds to the first projection 121, thereby allowing the first ring 11 engaging with the second ring 12 through the engagement between the first groove 1111 and the first projection 121. In the present embodiment, the first ring 11 and the second ring can be made of biocompatible materials, such as titanium alloy or silicone rubber.

In addition, the first ring 11 is further provided with a plurality of connecting walls 12, two adjacent walls of the plurality of connecting walls 112 are arranged in an interval, and the width of the interval may be substantially the same or slightly greater than that of one of the plurality of connecting walls 112. Furthermore, a second groove 1112 is provided on a sidewall of one of the connecting walls 112 facing the second ring 12. In the present embodiment, all the sidewalls, facing the second ring, of the connecting walls 112 are provided with second grooves 1112.

FIG. 3A to FIG. 3B show perspective views of a vascular fastener according to an embodiment of the present invention.

As shown in FIG. 3A to FIG. 3B (one end of the blood vessel 100 is fixed in the vascular fastener 1), the blood vessel 100 is first turned outward and attached to the first ring 11; then, the outwardly turned is fixed between the first ring 11 and the second ring 12 (as shown in FIG. 3B) through the engagement between the first groove 1111 and the first projection 121, thereby fixing the blood vessel 100 in the vascular fastener 1 efficiently.

FIG. 4A to FIG. 4B show perspective views of a vascular fastener according to an embodiment of the present invention.

As shown in FIG. 4A to FIG. 4B (the two vascular fasteners 1 are engaged with each other), by staggering the connecting walls 112 with each other, the two vascular fasteners 1 fixed with blood vessel 100 are engaged with each other through the engagement between the second groove 1112 and the second projection 1113 (which is provided on the first ring 11).

Figure 5:
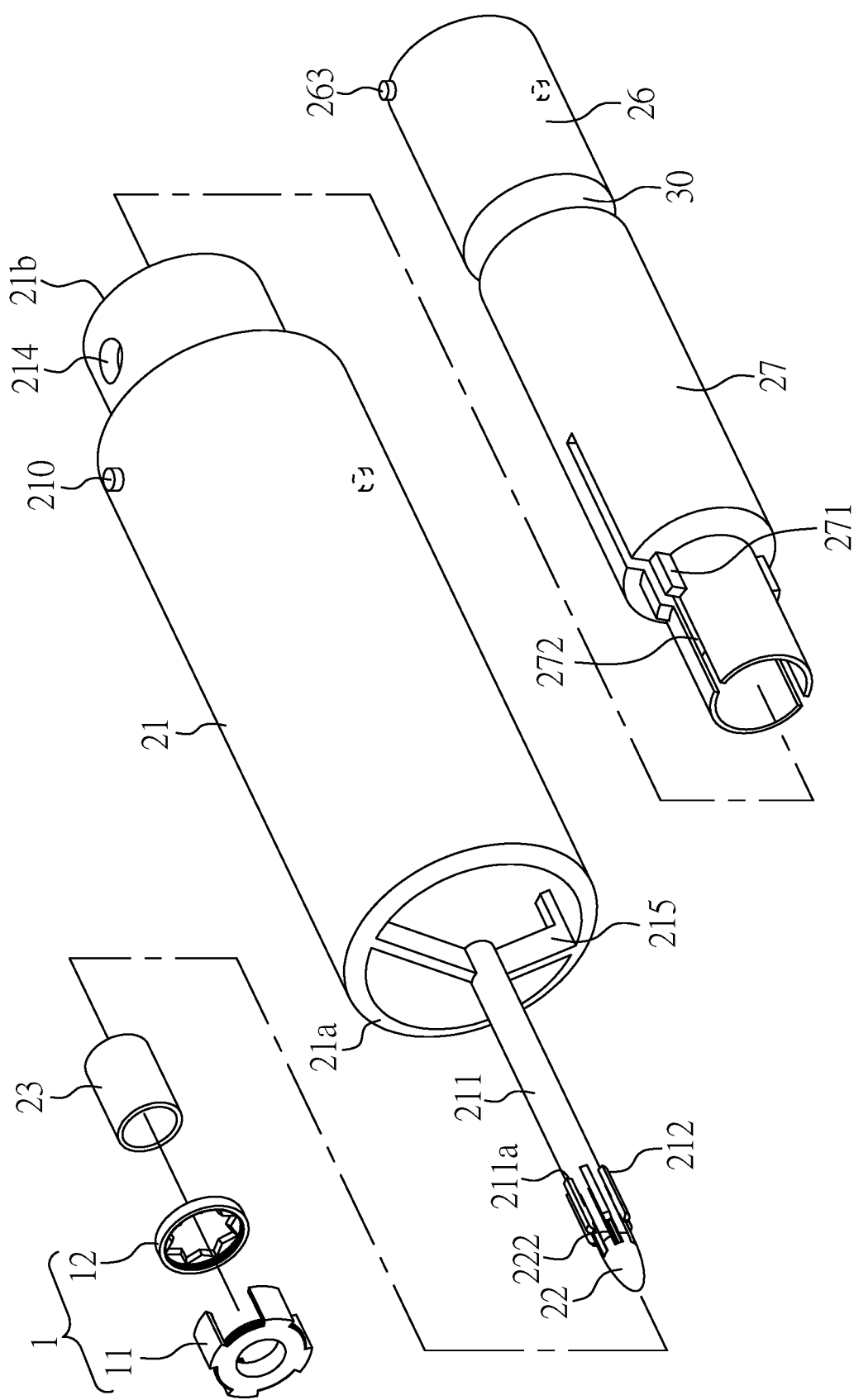
FIG. 5 shows an exploded view of a vascular fastening mechanism according to an embodiment of the present invention.

FIG. 5 shows an exploded view of a vascular fastening mechanism according to an embodiment of the present invention.

Figure 6:
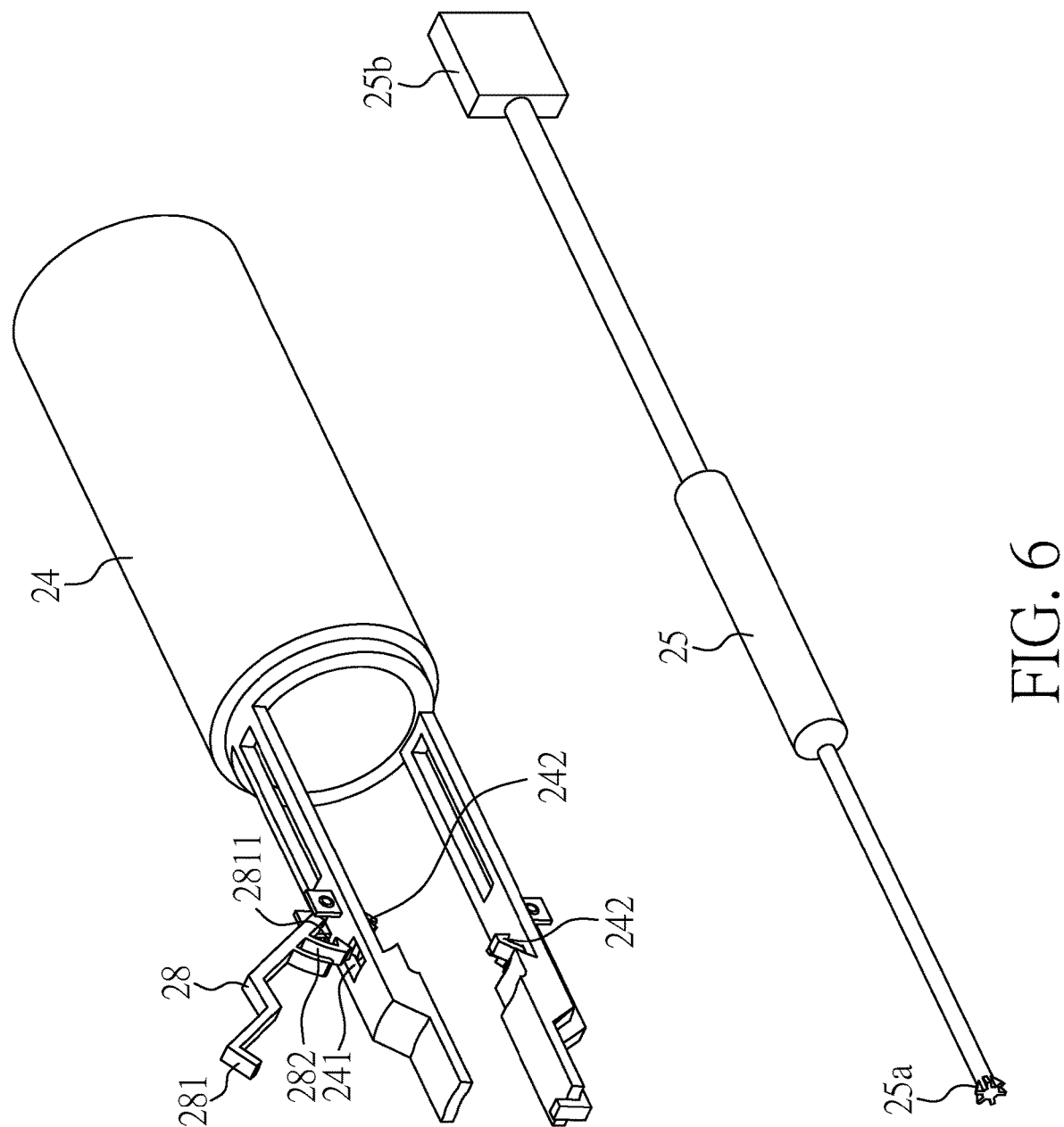
FIG. 6 shows a perspective view of a vascular fastening mechanism according to an embodiment of the present invention.

FIG. 6 shows a perspective view of a vascular fastening mechanism according to an embodiment of the present invention.

Figure 8:
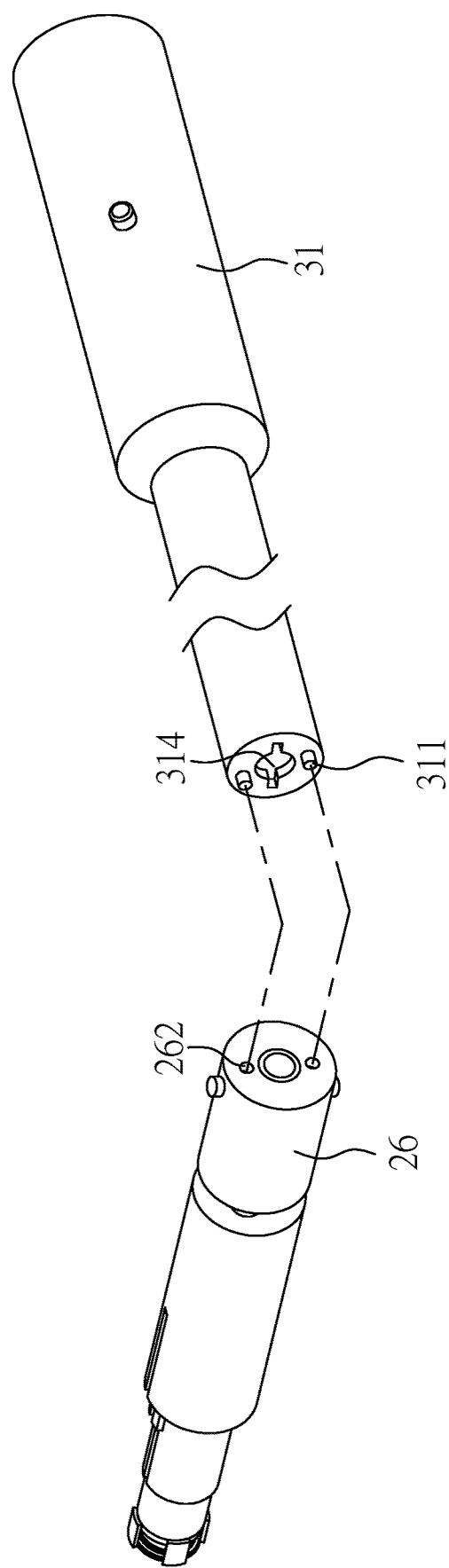
FIG. 8 shows an exploded view of the vascular anastomosis device according to an embodiment of the present invention.
Figure 13:
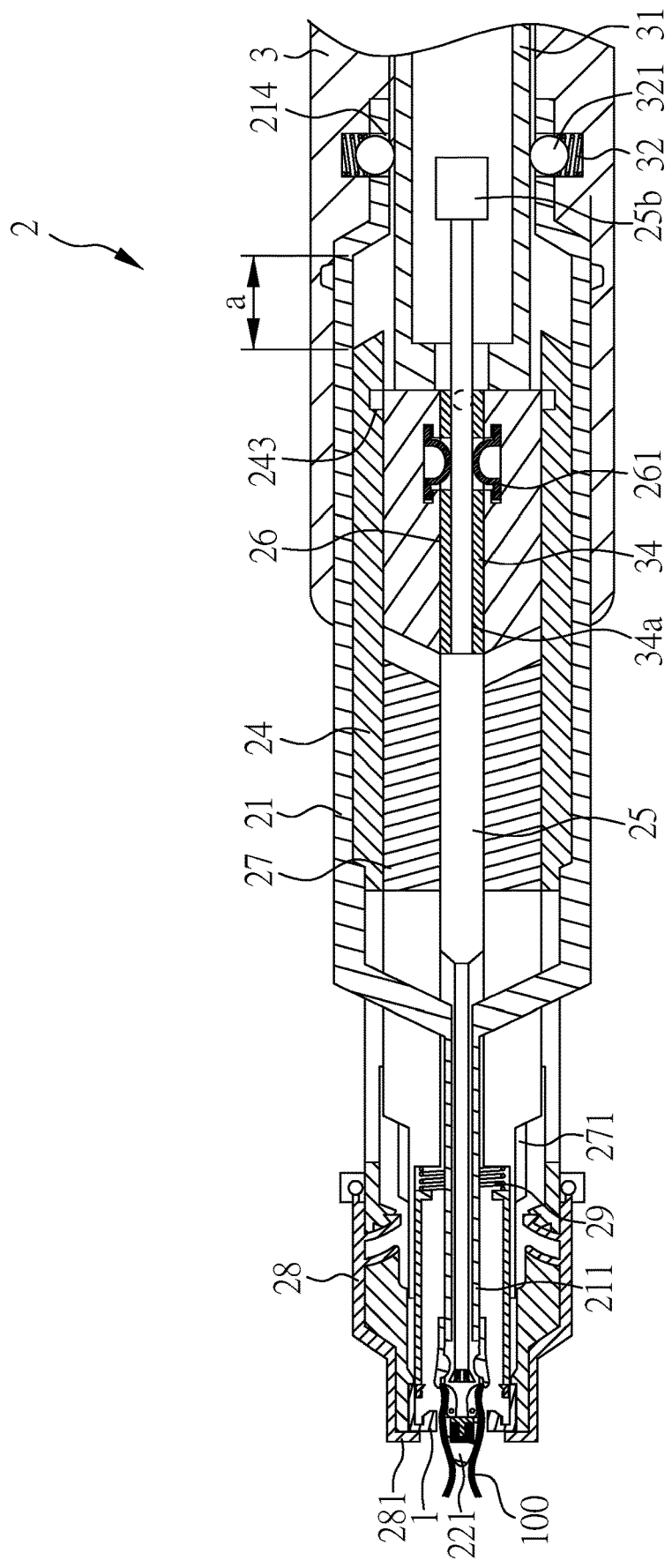
Figure 14:
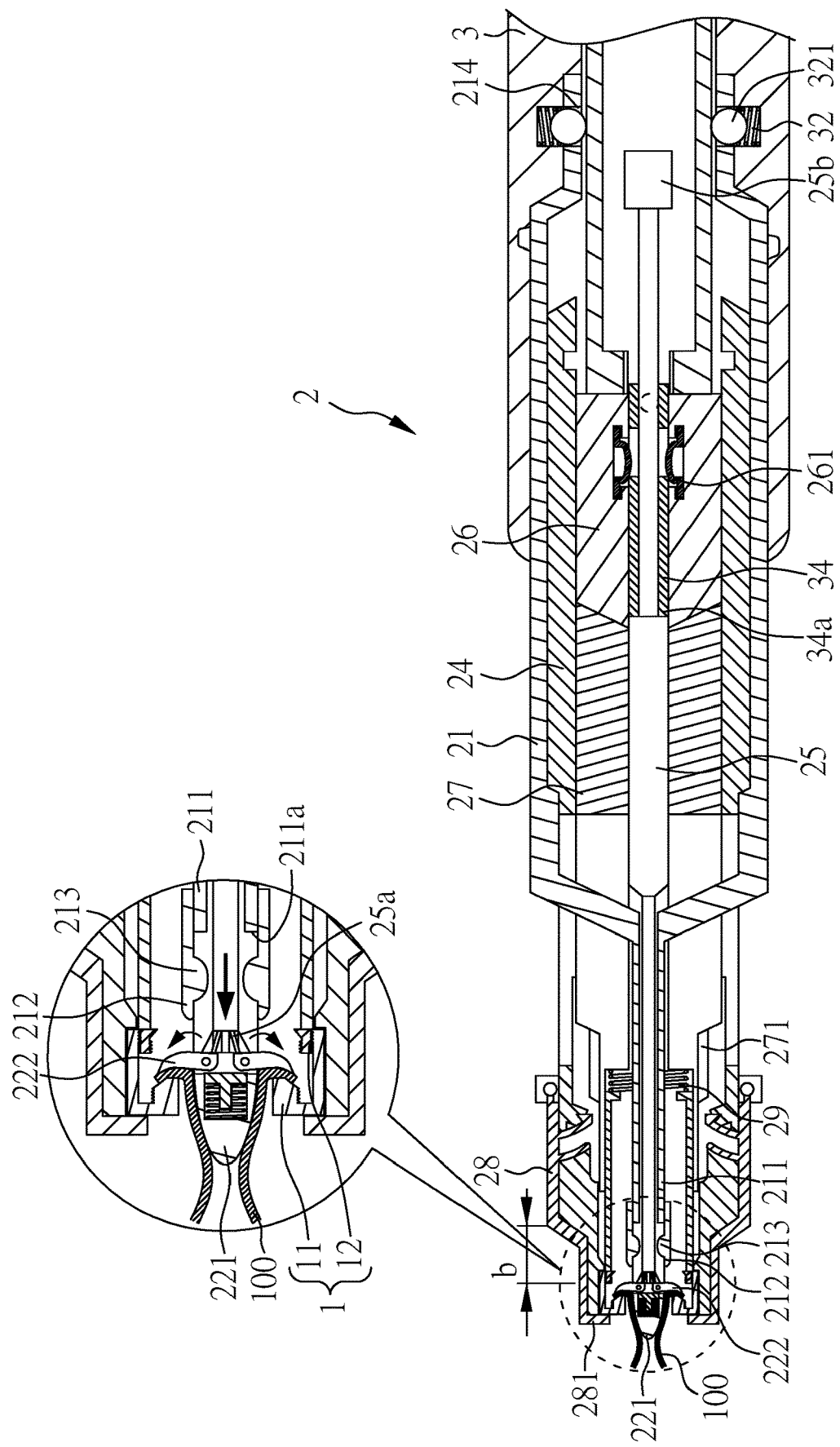
Figure 15:
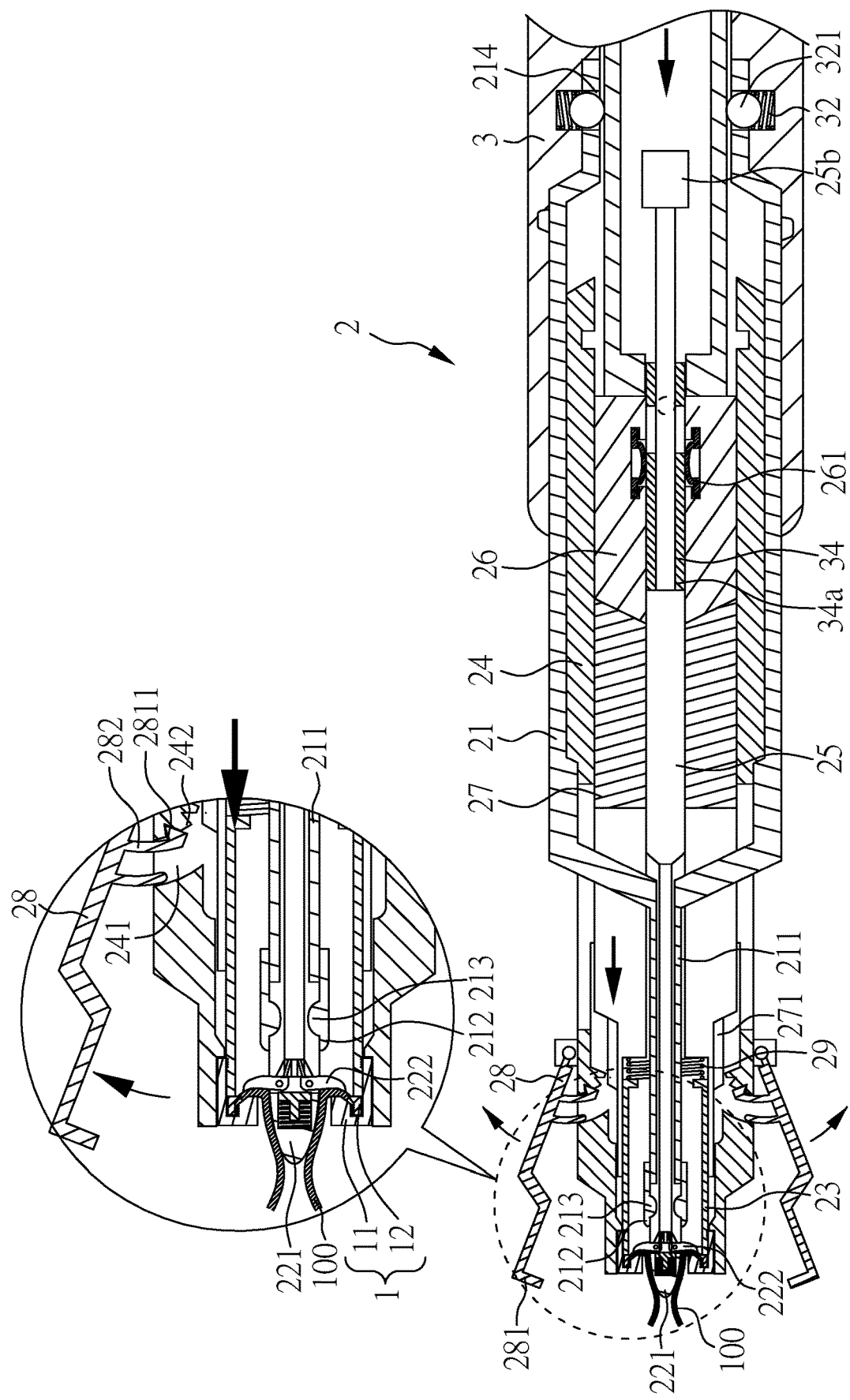
Figure 16:
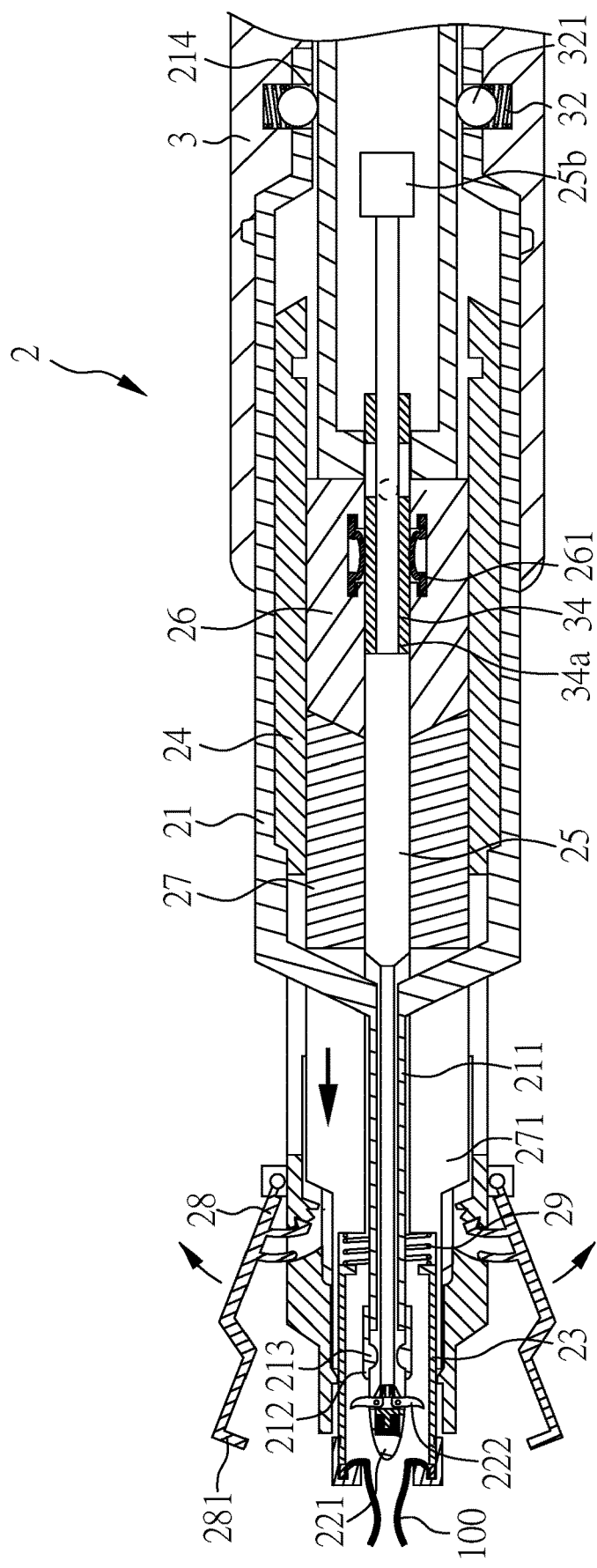

As shown in FIG. 5 and FIG. 6, the vascular fastening mechanism of the present embodiment includes: a first tube 21, a vascular supporting unit 22, an advancing ring 23, a third tube 24, and a spreading unit 25, in which the vascular fastener 1 is disposed in the vascular fastening mechanism 2. When operating the holding unit 4, the interlocking unit 313 moves along the wall of the through hole 41 to drive the advancing unit 31 (as shown in FIG. 1) to engage the advancing unit 31 with the first advancing tube 26 (as shown in FIG. 8), and the first advancing tube 26 can clamp and drive the hollow tube 34 by the first elastic element 261 (as shown in FIG. 10) simultaneously. Therefore, when the advancing unit 31 interlocks and moves the first advancing tube 26, the hollow tube 34 can be interlocked and moved at the same time. The hollow tube 34 keeps moving, and the front end 34a of the hollow tube 34 contacts the portion of spreading unit having a greater diameter to drive the spreading unit 25 (as shown in FIG. 13). Then, with the further movement, it allows the spreading unit 25 pushing the vascular spreader 222 to turn the blood vessel 100 outward (as shown in FIG. 14). While the fixation of the blood vessel 100 is completed, the engaging member 28 is loosened by the third flange (as shown in FIG. 15), thereby allowing the vascular fastener 1 leaving from the vascular anastomosis device 1000 (as shown in FIG. 16) to facilitate the subsequent procedure of fixing the other end of the blood vessel 100 in another vascular fastener 1 in the same manner. Hereinafter, the structure of the vascular fastening mechanism 2 will be described in more details.

Firstly, the first tube 21 is a hollow structure and is disposed between the third elastic element 32 and the advancing unit 31 (as shown in FIG. 10), the first end 21a of the first tube 21 is connected with the second tube 211, and thus the first end 21a has a connecting element 215 connected to the second tube 211. In addition, the second end 21b of the first tube 21 has a narrower diameter and is provided with a through hole 214, so that the housing 3 has enough space for arranging the third elastic element 32 (as shown in FIG. 10). Furthermore, the third elastic element 32 is disposed in the through hole 214, and an engaging element 321, which is a ball in the present embodiment, can be optionally used to engage the third elastic element 32 in the through hole 214 (as shown in FIG. 10). In addition, the other end 211a of the second tube 211 is provided with an elastic body 212, and the inner side of the elastic body 212 has a bulge 213 (for example, a semicircular bulge, a triangular bulge, or a circular bulge, but the present invention is not limited thereto), as shown in FIG. 10. When the spreading unit 25 disposed in the second tube 211 moves, the first end 25a of the spreading unit 25 can touch the bulge 213, so that the elastic body 212 is pushed outward and a gap is formed and the vascular supporting body 221 is sheathed into the blood vessel 100 at the same time, thereby clamping the blood vessel 100 on it (as shown in FIG. 11).

Secondly, the vascular supporting unit 22 is disposed at the other end 211a of the second tube 211 opposite to the end connected to the first end 21a. The vascular supporting unit 22 comprises a vascular supporting body 221 and a vascular spreader 222, the vascular spreader 211 is assembled on the vascular supporting body 221 (as shown in FIG. 10) and adjacent to the elastic body 212, and the vascular spreader 222 is rotatable. For example, the vascular spreader 222 rotates outwards by 90 degrees, while the present invention is not limited thereto, provided that an angle can be formed. Therefore, the spreading unit 25 can apply force on the vascular spreader 222 when the spreading unit 25 moves forward, such that the vascular spreader rotates outwards to turn the blood vessel 100, which is fixed on the vascular supporting unit 22, outward by an angle (for example, 90 degrees, and the angle of the present invention is subject to no particular limitation, provided that the angle can be formed), as shown in FIG. 14.

In addition, the first ring 11, the second ring 12, and the advancing ring 21 are disposed on the second tube 211 and between the vascular supporting unit 22 and the first end 21a, wherein the second ring 12 is located between the first ring 11 and the advancing ring 23, the first ring 11 is located between the vascular supporting unit 22 and the second ring 12, the advancing ring 23 is located between the second ring 12 and the first end 21a. The advancing ring 23 is a hollow cylinder and its thickness (that is, the thickness of the hollow cylinder) is set corresponding to that of the second ring 12; for example, the thickness of the advancing ring 23 is less than or equal to the thickness of the second ring 12, but the present invention is not limited thereto; thereby, it prevents the advancing ring 23 or the second ring 12 from contacting the intima of the blood vessel 100 when fixing the blood vessel 100 (as shown in FIG. 3A and FIG. 3B). Therefore, the second ring 12 can be interlocked when the advancing ring 23 moves forward, so that the second ring 12 is engaged with the first ring 11, thereby fixing the blood vessel 100 between the first ring 11 and the second ring 12. In addition, the pattern of the inner tube wall of the second ring 12 may be flower-shaped or star-shaped to provide a frictional force for the blood vessel 100 to be clamped.

In addition, the third tube 24 is disposed in the first tube 21 and protruding from the first end 21a, wherein the second tube 211, the first ring 11, the second ring 12 and the advancing ring 23 are disposed in the third tube 24. A through hole 241 is provided on a tube wall of the third tube 24, and the engaging member 28 has a first protrusion 282 provided in the through hole 241. In addition, the through hole 241 of the third tube 24 includes a second protrusion 242, the first protrusion 282 has a first recess 2811, and the first recess 2811 and the second protrusion 242 are disposed correspondingly. Therefore, when the third flange 271 moves forward, it pushes the first protrusion 282, so that the first protrusion 282 can be detached to release the vascular fastener 1, wherein the first protrusion 282 is originally engaged with the first recess 2811 through the second protrusion 242 to be engaged in the through hole 241, as shown in FIG. 15.

Lastly, the spreading unit 25 is disposed in the third tube 24, and the first end 25a of the spreading unit 25 is convex or multi-claw type (for example, cone or six-claw type) and is adjacent to the vascular spreader 222 in favor of spreading the elastic body 212 of the second tube 211, so that the blood vessel 100 can be clamped on the vascular supporting unit 22.

The vascular fastening mechanism of the present embodiment further includes a first advancing tube 26 and a second advancing tube 27, wherein both of the first advancing tube 26 and the second advancing tube 27 are disposed in the third tube 24. The spreading unit 25 is disposed in the first advancing tube 26 and the second advancing tube 27, the second advancing tube 27 is located between the first advancing tube 26 and the first end 21a, and the first half of the second advancing element 27 is provided with a channel 272 to ensure that the second advancing element 27 can move on the connecting element 215 of the first tube 21 so as to protrude from the first tube 21.

In addition, there is a gap 30 between the first advancing element 26 and the second advancing element 27 to provide the spreading unit 25 with enough moving space.

Furthermore, the diameter of the second advancing element 27 is changed from small to large, and a third flange 271 is provided where the tube diameter becomes larger. When the second advancing element 27 moves forward, the third flange 271 can push the first protrusion 282 of the engaging member 28 to make the engaging member 28 spring to loosen the first flange 281, thereby releasing the vascular fastener 1 (as shown in FIG. 15).

The vascular fastening mechanism further includes an engaging member 28 assembled on an outer sidewall of the third tube 24, the engaging member 28 has a first flange 281, and the first ring 11, the second ring 12 and the advancing ring 23 are secured in the third tube 24 through the first flange 281. When the engaging member 28 springs, the first flange 281 no longer fixes the first ring 11, the second ring 12 and the advancing ring 23, so that the vascular fastener 1 can be released, and the vascular fastener 1 can be distant from the vascular anastomosis device 1000.

Figure 7:
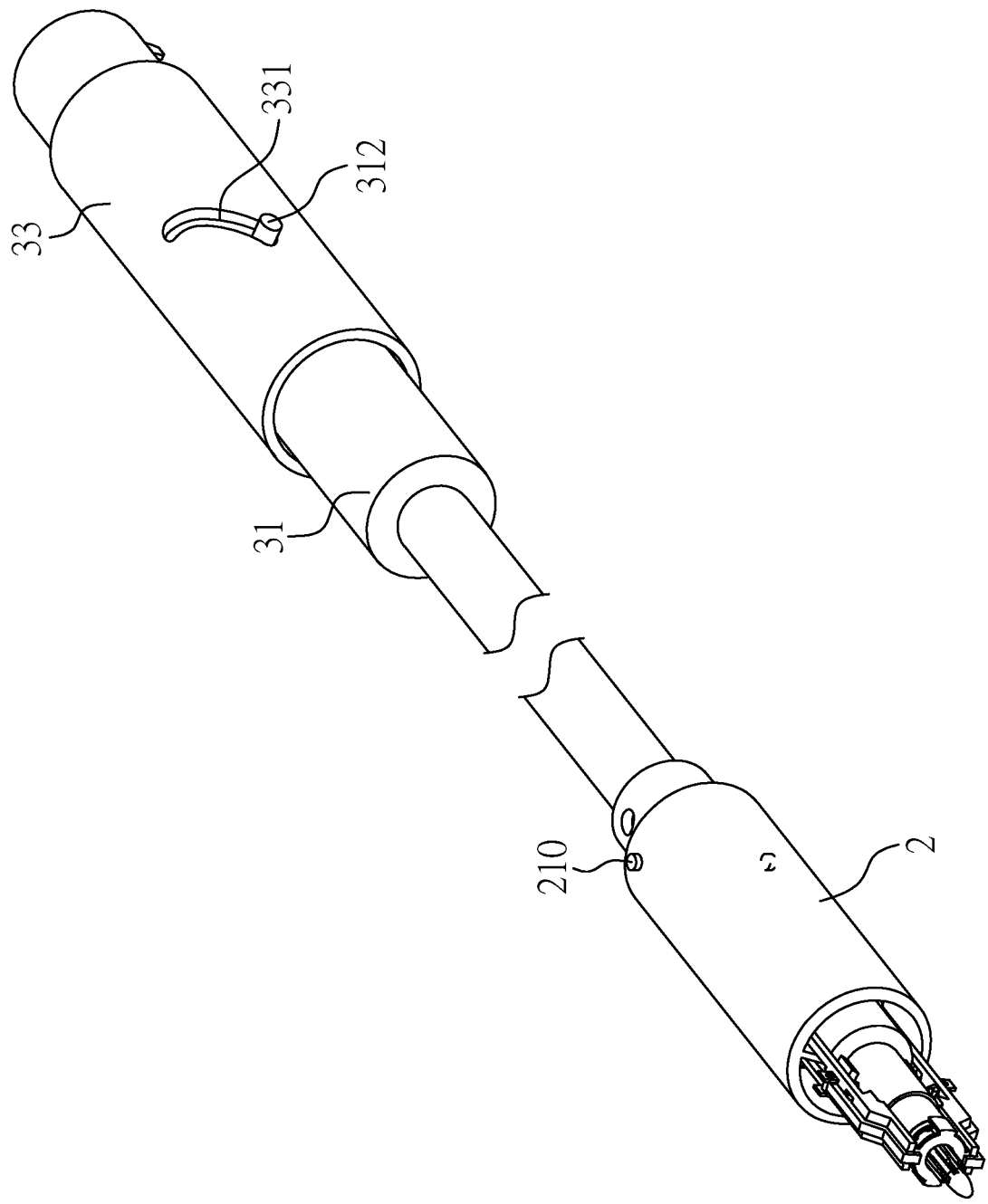
FIG. 7 shows an enlarged perspective view of the combination of the vascular fastener, the advancing unit, and the fourth tube in FIG. 1.

FIG. 7 shows an enlarged perspective view of the combination of the vascular fastener 2, the advancing unit 31, and the fourth tube 33 in FIG. 1.

As shown in FIG. 1 and FIG. 7, in the vascular fastening mechanism of the present embodiment, a fourth tube 33 is further disposed in the housing 3, and the advancing unit 31 is disposed in the fourth tube 33; wherein, the fourth tube 33 has a first track 331, and the advancing unit 31 has a fourth protrusion 312 disposed on the first track. Therefore, when the holding unit 4 is pressed, the interlocking unit 313 will move along the wall of the through hole 41, thereby driving the advancing unit 313; and, the advancing unit 31 rotates at the same time, because the fourth protrusion 312 is engaged with the first track 33.

FIG. 8 shows an exploded view of the vascular anastomosis device according to an embodiment of the present invention.

Figure 9:
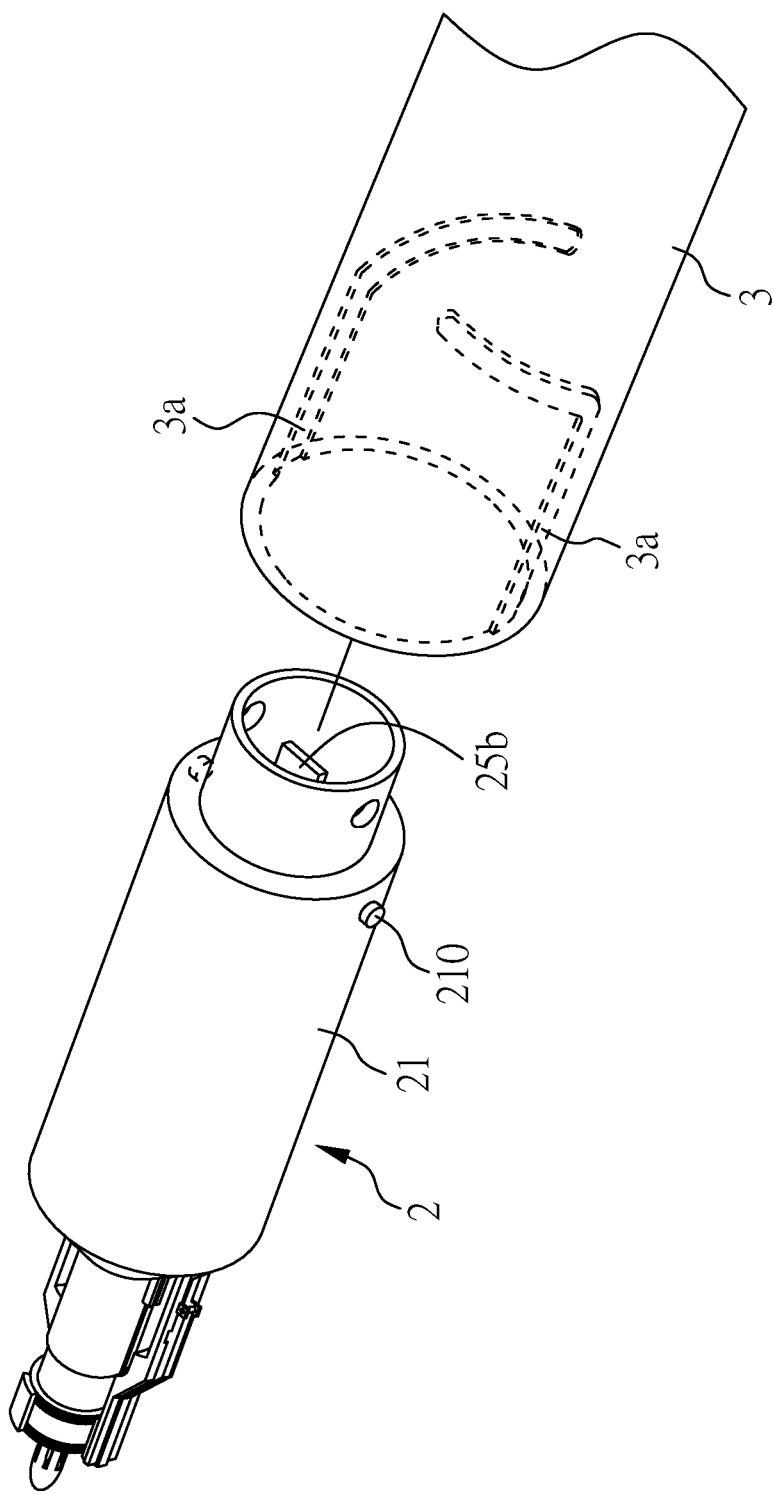
FIG. 9 shows an exploded view of the vascular fastening mechanism and the housing in FIG. 1.

FIG. 9 shows an exploded view of the vascular fastening mechanism and the housing in FIG. 1.

FIG. 10 shows a cross-sectional view of a vascular fastening mechanism according to an embodiment of the present invention.

As shown in FIG. 5, FIG. 8 and FIG. 10, in the vascular fastening mechanism of the present embodiment, the advancing unit 31 and a second end 21b of the first tube 21 are disposed correspondingly. It refers to diameter of the advancing unit 31 is smaller than or equal to that of the second end 21b of the first tube 21, allowing the advancing unit 31 can be disposed in the first tube 21 and can be moved arbitrarily. In addition, the advancing unit 31 and the first advancing tube 26 are disposed correspondingly.

In the vascular fastening mechanism of the present embodiment, the advancing unit 31 has a third protrusion 311, the first advancing tube 26 has a second recess 262, and the third protrusion 311 corresponds to the second recess 262. Therefore, the third protrusion 311 can be engaged with the second recess 262, so that the first advancing tube 26 can be interlocked to the advancing unit 31 (for example, they can rotate and/or move synchronously).

In the vascular fastening mechanism of the present embodiment, a third elastic element 32 (as shown in FIG. 10) is further disposed in the housing 3, and the elastic element 32 can be a spring, an elastic piece, and the like. In addition, the first tube 21 is disposed between the third elastic element 32 and the advancing unit 31, thereby fixing the first tube 21 on the housing 3.

As shown in FIG. 6 and FIG. 9, in the vascular fastening mechanism of the present embodiment, the second end 25b of the spreading unit 25 is a sheet structure, and the second end 25b and the through hole 31 of the advancing unit 31 are disposed correspondingly, as shown in FIG. 8. Therefore, the second end 25b of the spreading unit 25 disposed in the first tube 21 can pass through the through hole 314, thereby being disposed in the advancing unit 31, as shown in FIG. 8 and FIG. 10. Furthermore, the second track 3a provided on the housing 3 and the second bump 210 on the first tube 21 are disposed correspondingly. Therefore, the vascular fastening mechanism 2 can be engaged in the housing 3 along the second track 3a; and, the vascular fastening mechanism 2 of different sizes can be applied based on the blood vessel of different sizes.

As shown in FIG. 10, in the vascular fastening mechanism of the present embodiment, a first elastic element 261 is further disposed on an inner tube wall of the first advancing tube 26, which can be a spring or an elastic piece, the first elastic element 261 is disposed between the hollow tube 34 and the first advancing tube 26, and the first elastic element 261 is used to clamp or loosen the hollow tube 34. The hollow tube 34 can move with the first advancing tube 26 when the first elastic element 261 clamps the hollow tube 34. Therefore, when the front end 34a of the hollow tube 34 touches the place where the tube diameter of the spreading unit 25 becomes larger, the spreading unit 25 can be driven, as shown in FIG. 13. On the contrary, if the first elastic element 261 loosens the hollow tube 34, the hollow tube 34 cannot move with the first advancing tube 26, as shown in FIG. 15. Thereby, whether moving the spreading unit 25 or not can be regulated.

The vascular fastening mechanism of the present embodiment further includes a second elastic element 29, which is a spring, elastic piece and the like, and the second elastic element 29 is disposed on an outer sidewall of the second tube 211 and connected with the advancing ring 23. When the first flange 281 of the engaging member 28 no longer fixes the first ring 11, the second elastic member 29 can provide a force to push the ring 23 outward, and keep the vascular fastener away from the vascular anastomosis device 1000.

In the vascular fastening mechanism of the present embodiment, the first advancing tube 26 has a second flange 263, a groove 243 is provided on the inner tube wall of the third tube 24, and the second flange 263 corresponds to the groove 243. The groove 243 is an L-shaped groove. Therefore, whether the advancing tube 26 can drive the third tube 24 to move together or not depends on the different positions of the groove 243 where the second flange 263 engages.

Operating Mechanism of the Vascular Anastomosis Device

FIG. 10 to FIG. 16 show schematic diagrams of the operating mechanism of the vascular anastomosis device according to an embodiment of the present invention.

As shown in FIG. 10 (showing the inactive state of the vascular anastomosis device 1000), the third protrusion 311 of the advancing unit 31 has not yet been engaged with the second recess 262 of the first advancing tube 26. In addition, the blood vessel 100 is not clamped on the vascular supporting body 221 either. Furthermore, the second flange 263 of the first advancing tube 26 is engaged with the groove 243 on the inner wall of the third tube 24. The groove 243 is an L-shaped groove, that is, the second flange 263 can only rotates in the groove 243 in the beginning; and, the second flange 263 can move forward only when the second flange 263 rotates to a 90-degree right angle of the groove 243. Therefore, if the first advancing tube 26 moves under force, the third pipe 24 can be driven to move synchronously (because the second flange 263 is engaged in the region of the groove 243 that cannot move forward and backward). However, if the first advancing tube 26 rotates greater than a specific angle (that is, after the second flange 263 rotates to the 90-degree right angle of the groove 243), the first advancing tube 26 will not will not drive the third tube 24 to move synchronously; and, it is because the second flange 263 is engaged in the region of the groove 243 that can move back and forth, the first advancing tube 26 can move forward alone. In addition, the first elastic element 261 of the inner tube wall of the first advancing tube 26 clamps the hollow tube 34, so the hollow tube 34 can be driven synchronously when the first advancing tube 26 moves.

As shown in FIG. 11, first, the blood vessel 100 is sleeved on the vascular supporting body 221 from the front end, and is engaged with the elastic body 212. Then the movable unit 5 is operated to rotate the interlocking rod 35 with the shaft 351 as the center, such that the interlocking rod 35 contact the first bump 330 under the fourth tube 33 to interlock the advancing unit (as shown in FIG. 1) and the spreading unit 25 is driven to move backward. Thereby, it allows the first end 25a (for example, cone-shaped or six-claw type) of the spreading unit 25 squeezing the bulge 213 disposed in the elastic body 212 to spread the elastic body 212 outward. Then the blood vessel 100 is clamped in the elastic body 212 and is fixed by the front edge of the elastic body 212. In addition, the movable unit 5 can be repeatedly operated until the blood vessel 100 is clamped in the elastic body 212 in a correct manner.

Figure 12:
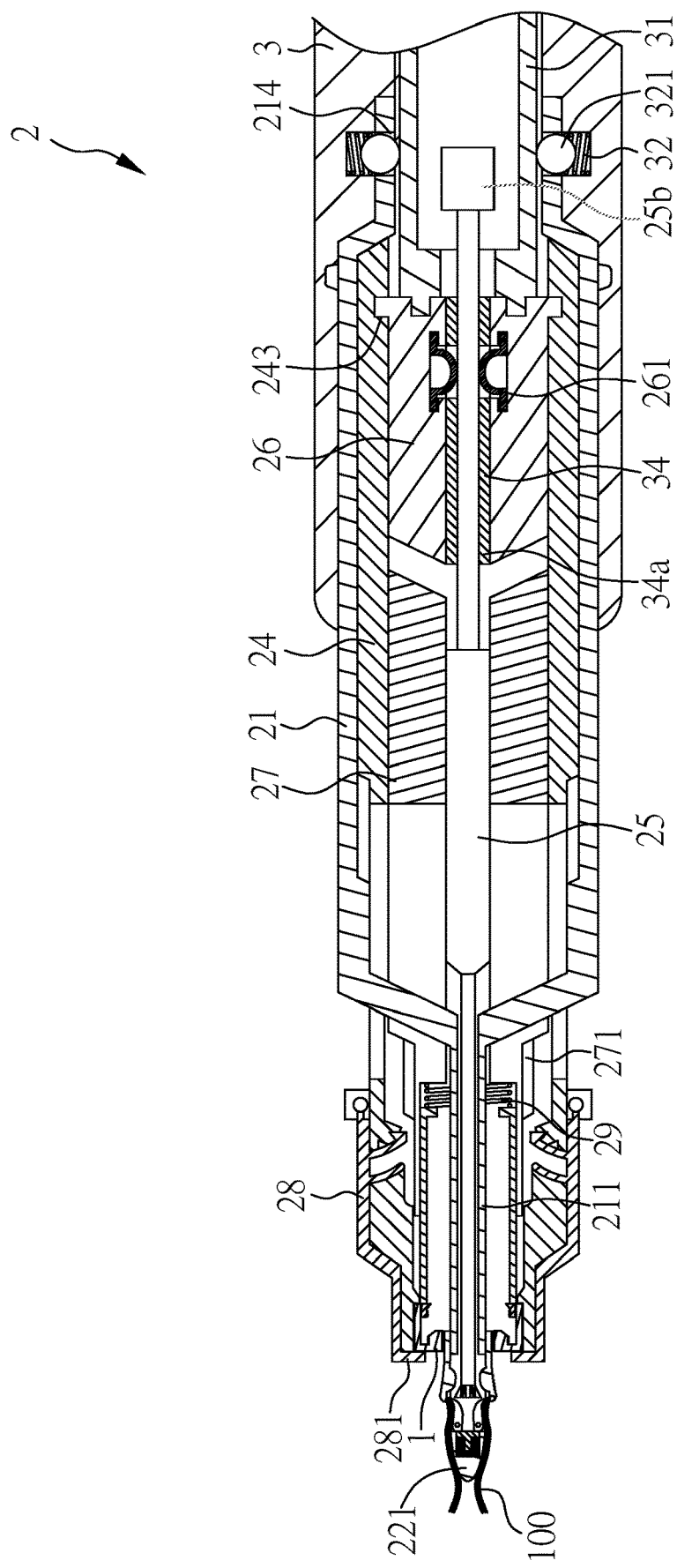

As shown in FIG. 12, the advancing unit 31 (as shown in FIG. 1) is driven by the action of the interlocking unit 313 and the through hole 41 through operating the holding unit 4. At this moment, the third protrusion 311 of the advancing unit 31 is only engaged with the second recess 262 of the first advancing tube 26, but the first advancing tube 26 has not been pushed yet.

As shown in FIG. 13, the holding unit 4 is continuously operated, and the interlocking unit 313 and the through hole 41 are actuated to drive the advancing unit 31 (as shown in FIG. 1), thereby interlocking the first advancing tube 26 to move forward by a first distance a, and synchronously drive the third tube 24 to move forward by a first distance a (because the second flange 263 is engaged in the rotatable groove 243). Therefore, the third tube 24 wraps and clamps part of the blood vessel 100 in the vascular fastener 1. In addition, the first advancing tube 26 can be interlocked to the hollow tube 34 by the first elastic element 261, so the first advancing tube 26 moves forward, allowing the hollow tube 34 moving forward synchronously to let the front end 34a contact the spreading unit 25 at the position where the diameter of the spreading unit becomes larger. Therefore, the spreading unit 25 is interlocked to move. At the same time, the fourth protrusion 312 of the advancing unit 31 is engaged with the first track 331 of the fourth tube 33 (as shown in FIG. 7) and the fourth protrusion 312 is also engaged with the third track 3b (as shown in FIG. 1) disposed in the housing 3, so the advancing unit 31 first moves forward and then turns along the first track 331 (as shown in FIG. 7). In addition, the third protrusion 311 is engaged with the second recess 262, so the advancing unit 31 can interlock the first advancing tube 26 to rotate (as shown in FIG. 12; and since FIG. 13 shows the condition that it has begun to rotate, the cross-sectional view of FIG. 13 is not disclosed), thereby allowing the second flange 263 of the first advancing tube 26 rotating to a region of the groove 243 that can move back and forth. Therefore, the first advancing tube 26 no longer moves synchronously with the third tube 24. Finally, the advancing unit 31 can continue to move forward after rotating, and thus the first advancing tube 26 can move forward alone.

As shown in FIG. 14, the holding unit 4 is continuously operated to make the first advancing tube 26 continue to move forward. However, because the first advancing tube 26 no longer interlocks with the third tube 24, it is only interlocked with the hollow tube 34 by the first elastic element 261. Therefore, in the process that the first advancing tube 26 moves forward by a second distance b (that is, the first advancing tube 26 moves to the position where it contacts the second advancing tube 27), the hollow tube 34 has contacted the spreading unit 25 at the position where the diameter of the spreading unit 25 becomes larger, so the spreading unit 25 is driven to move by the second distance b at the same time, allowing the spreading unit 25 applying force on the vascular spreader 222. As a result, the vascular spreader 222 turns the blood vessel 100 outward by an angle (for example, 90 degrees, and the degrees of the angle of the present invention is subject to not particular limitation, provided that an angle can be formed), thereby attaching the blood vessel 100 to the first ring 11 to facilitate subsequent use of the second ring 12 to fix the blood vessel 100 on the first ring 11.

As shown in FIG. 15, the first advancing tube 26 continues to move due to the continuous operation of the holding unit 4. At the same time, the first elastic element 261 has been loosened, so the hollow tube 34 will not follow the first advancing tube 26 to move. Therefore, the first advancing tube 26 only drives the second advancing tube 27 to move forward, so that the advancing ring 23 applies force to the second ring 12 to engage the second ring 12 with the first ring 11 fixed with the blood vessel 100. Meanwhile, the third flange 271 on the second advancing tube 27 will lightly contact the first protrusion 282 of the engaging member 28, so that the first protrusion 282, which is originally engaged in the through hole 241 through the engagement between the second protrusion 242 and the first recess 2811, can be disengaged. Since the engaging member 28 springs, the first flange 281 no longer fixes the first ring 11, the second ring 12, and the advancing ring 23. Thereby, the vascular fastener 1 can be detached from the vascular anastomosis device 1000.

As shown in FIG. 16, the second elastic element 29 provides the advancing ring 21 with an outward spring force to detach the blood fastener 1 from the vascular anastomosis device 1000. Then, after the vascular fastener 1 is far away, another vascular fastener 1 can be inserted into the vascular fastening mechanism 2, or the entire vascular fastening mechanism 2 can be replaced with a vascular fastening mechanism 2 inserted with another vascular fastener 1 in order to repeat the above steps to fix the other end of the blood vessel 100 to another vascular fastener 1. Finally, the two vascular fasteners 1 are engaged with each other to complete the anastomosis of the blood vessel 100.

Although the present invention has been explained in relation to its preferred embodiment, it is to be understood that many other possible modifications and variations can be made without departing from the spirit and scope of the invention as hereinafter claimed.

What is claimed is:

1. A vascular anastomosis device, comprising: a vascular fastener, comprising a first ring and a second ring, wherein the first ring is provided with a first groove, the second ring is provided with a first projection, and the first groove corresponds to the first projection; a vascular fastening mechanism, wherein the vascular fastener is disposed in the vascular fastening mechanism and the vascular fastening mechanism comprises: a first tube, wherein a first end of the first tube is connected to a second tube; a vascular supporting unit, disposed at the other end of the second tube opposite to the end connected to the first tube, wherein the vascular supporting unit comprises a vascular supporting body and a vascular spreader, and the vascular spreader is assembled on the vascular supporting body; an advancing ring, wherein the first ring, the second ring, and the advancing ring are disposed on the second tube and between the vascular supporting unit and the first end, the second ring is located between the first ring and the advancing ring, the first ring is located between the vascular supporting unit and the second ring, and the advancing ring is located between the second ring and the first end; a third tube, disposed in the first tube and protruding from the first end, wherein the second tube, the first ring, the second ring and the advancing ring are disposed in the third tube; and a spreading unit, disposed in the third tube, wherein one end of the spreading unit is adjacent to the vascular spreader.

2. The vascular anastomosis device of claim 1, wherein the vascular fastening mechanism further comprises a first advancing tube disposed in the third tube, and the spreading unit is disposed in the first advancing tube.

3. The vascular anastomosis device of claim 2, wherein the vascular fastening mechanism further comprises a second advancing tube, the second advancing tube is disposed in the third tube, the spreading unit is disposed in the second advancing tube, and the second advancing tube is located between the first advancing tube and the first end.

4. The vascular anastomosis device of claim 2, wherein a first elastic element is further disposed on an inner tube wall of the first advancing tube, the first elastic element is disposed between the spreading unit and the first advancing tube.

5. The vascular anastomosis device of claim 2, further comprising a housing, wherein an advancing unit is disposed in the housing, the vascular fastening mechanism is disposed in the housing, and the advancing unit and the first advancing tube are disposed correspondingly.

6. The vascular anastomosis device of claim 5, wherein the advancing unit has a third protrusion, the first advancing tube has a second recess, and the third protrusion corresponds to the second recess.

7. The vascular anastomosis device of claim 5, wherein a fourth tube is further disposed in the housing, and the advancing unit is disposed in the fourth tube; wherein, the fourth tube has a first track, and the advancing unit has a fourth protrusion disposed on the first track.

8. The vascular anastomosis device of claim 2, wherein the first advancing tube has a second flange, a groove is provided on the inner tube wall of the third tube, and the second flange corresponds to the groove.

9. The vascular anastomosis device of claim 1, wherein the vascular fastening mechanism further comprises an engaging member assembled on an outer sidewall of the third tube, the engaging member has a first flange, and the first ring, the second ring and the advancing ring are fixed in the third tube through the first flange.

10. The vascular anastomosis device of claim 9, wherein a through hole is provided on a tube wall of the third tube, and the engaging member has a first protrusion disposed in the through hole.

11. The vascular anastomosis device of claim 10, wherein the through hole of the third tube comprises a second protrusion, the first protrusion has a first recess, and the first recess and the second protrusion are arranged correspondingly.

12. The vascular anastomosis device of claim 1, wherein the vascular fastening mechanism further comprises a second elastic element, and the second elastic element is disposed on an outer sidewall of the second tube and connected with the advancing ring.

13. The vascular anastomosis device of claim 1, further comprising a housing, wherein an advancing unit is disposed in the housing, the vascular fastening mechanism is disposed in the housing, and the advancing unit and a second end of the first tube are disposed correspondingly.

14. The vascular anastomosis device of claim 13, wherein a third elastic element is further disposed in the housing, and the first tube is disposed between the third elastic element and the advancing unit.

15. The vascular anastomosis device of claim 13, further comprising a holding unit, wherein the holding unit is located in the housing and connected to the advancing unit.

16. The vascular anastomosis device of claim 1, wherein a plurality of connecting walls are further disposed on the first ring, and two adjacent walls of the plurality of connecting walls are arranged in an interval.

17. The vascular anastomosis device of claim 16, wherein the width of the interval is substantially the same as that of one of the plurality of connecting walls.

18. The vascular anastomosis device of claim 16, wherein a second groove is provided on a sidewall of one of the plurality of connecting walls facing the second ring.

* * * * *